United States Patent [19]

Howard, III et al.

[11] Patent Number: 5,569,267
[45] Date of Patent: Oct. 29, 1996

[54] DEVICE AND METHODS FOR PARIETO-OCCIPITAL PLACEMENT OF VENTRICULAR CATHETERS

[75] Inventors: Matthew A. Howard, III, Iowa City, Iowa; M. Sean Grady, Mercer Island; H. Richard Winn, Seattle, both of Wash.

[73] Assignee: University of Washington, Seattle, Wash.

[21] Appl. No.: 207,476

[22] Filed: Mar. 4, 1994

[51] Int. Cl.$^6$ ............................................. A61B 19/00
[52] U.S. Cl. ................................................. 606/130
[58] Field of Search ................................ 128/657, 658, 128/772; 606/129, 130

[56] References Cited

U.S. PATENT DOCUMENTS

| | | | |
|---|---|---|---|
| 3,053,256 | 9/1962 | Cooper et al. | 606/130 |
| 3,223,087 | 12/1965 | Vladyka et al. | 606/130 |
| 4,386,602 | 6/1983 | Sheldon et al. | 606/130 |
| 4,397,307 | 8/1983 | Keller | 606/130 |
| 4,613,324 | 9/1986 | Ghajar | 606/130 |
| 4,860,331 | 8/1989 | Williams et al. | 606/130 |
| 5,030,223 | 7/1991 | Anderson et al. | 606/130 |

FOREIGN PATENT DOCUMENTS

| | | |
|---|---|---|
| 1456100 | 3/1985 | U.S.S.R. . |
| 2258153 | 2/1993 | United Kingdom . |

OTHER PUBLICATIONS

Ghajar, "A Guide for Ventricular Catheter Placement", *J. Neurosurg.* 63:985–986 (Dec., 1985).
Dan et al., "The Incidence of Epilepsy After Ventricular Shunting Procedures", *J. Neurosurg.* 65:19–21 (Jul., 1986).
Albright et al., "Function of Parietal and Frontal Shunts in Childhood Hydrocephalus", *J. Neurosurg.* 69:883–886 (Dec., 1988).
Manwaring, "Endoscope–Guided Placement of the Ventriculoperitoneal Shunt", *Neuroendoscopy* 1:29–40 (1992).

*Primary Examiner*—Max Hindenburg
*Attorney, Agent, or Firm*—Townsend and Townsend and Crew

[57] ABSTRACT

The present invention relates to devices and methods for placement of ventriculoperitoneal shunts in human patients. More particularly, the present invention provides means for accurate and safe placement of ventriculoperitoneal shunts from a posterior approach.

9 Claims, 4 Drawing Sheets

DEVICE AND METHODS FOR PARIETO-OCCIPITAL PLACEMENT OF VENTRICULAR CATHETERS

BACKGROUND OF THE INVENTION

The present invention relates to devices and methods for placement of ventriculoperitoneal shunts in human patients. More particularly, the present invention provides means for accurate and safe placement of ventriculoperitoneal shunts from a posterior approach.

Ventriculoperitoneal (VP) shunt placement for hydrocephalus is one of the most common procedures in neurological surgery. Hydrocephalus may result from subarachnoid hemorrhage, trauma, tumors, and the like. The technique entails introducing a catheter through brain tissue into one of the lateral ventricles of the brain. Cerebrospinal fluid in the ventricle may be vented through the catheter to relieve signs, symptoms, and sequelae of hydrocephalus.

The current surgical technique for placement of VP shunts was developed in the 1950's by Scarff and has persisted with few modifications. Despite the relative simplicity of this procedure, the complication rate can be significant and includes operative morbidity as well as post-operative infections, and obstructions, etc. Surgical technique plays a major role in reducing complications associated with VP shunts. Improper placement of the ventricular catheter may result in neurologic injury from the misplaced catheter or may cause an early proximal shunt obstruction, which is often secondary to blockage by adherent choroid plexus and other debris. The incidence of misplaced catheters is variable and dependent on a variety of factors, including the experience of the surgeon, the size of the targeted ventricle, the surgical approach and the use of intraoperative guidance, such as fluoroscopy, ultrasound, or endoscopy. Thus, to optimize shunt function and minimize morbidity proper placement of the proximal catheter is essential.

Two surgical approaches have been be used for VP shunt placement, frontal and parieto-occipital. Although little data is available, a retrospective series by Albright et al., *J. Neurosurg.* 69:883–886 (1988), found good catheter placement in only 55% of frontal shunts and 33% of parieto-occipital shunts. Four cases of ophthalmic injury following ventricular catheter insertion were reported recently and intracerebral hemorrhages secondary to misplacement have appeared in isolated clinical reports, but the rate of such complications is not known. Recently, endoscopic placement of ventricular catheters has been reported with an accurate placement rate of 90%. *Neuroendoscopy*: Volume 1, Mary Ann Liebert, New York, pp. 29–40 (1992). The disadvantages of this technique are related to the cost of the instrumentation, the added operative time, and the time required for the surgeon to become familiar with the technique. If, however, an accurate, rapid and inexpensive tool were available to aid in catheter placement, it would simplify the procedure.

A frontal catheter guide fulfilling these criteria has been successfully developed by Ghajar for placement of frontal ventricular catheters. Ghajar JB, *J. Neurosurg.* 68:318–319(1988). This instrument capitalized on the anatomical observation that a line passing perpendicular to the skull at the coronal suture will intersect the lateral ventricle.

However, parieto-occipital catheter placement has significant advantages over frontal catheter placement. The catheter path necessary for the frontal approach to the ventricles traverses frontal lobe regions having a low seizure threshold. Mechanical irritation of the neural tissue surrounding the catheter may give rise to epileptogenic foci independent of the underlying cause of hydrocephalus. This complicates patient management and increases health care cost, as well as markedly impacting the patient's quality of life.

The anatomy of the head and neck also cause technical difficulties for the surgeon. The distal end of the shunt is subcutaneously tunneled to the peritoneal cavity for implantation. Implantation in the open peritoneum provides an outlet for excess fluid drainage from the ventricles. The catheter path to the abdomen is circuitous from the frontal burr hole, however. The tube must pass posterior to the ear, and generally requires an additional skin incision. These difficulties increase operative time, cost, and complications.

What is needed in the art are devices and methods for accurate placement of VP shunt catheters by the parieto-occipital approach. The devices and methods should be easy for clinicians to learn and use. Optimally, expensive intraoperative imaging procedures should not be necessary. Quite surprisingly, the present invention fulfills these and other related needs.

SUMMARY OF THE INVENTION

The present invention provides devices for parieto-occipital placement of a ventricular catheter in a brain. The devices generally comprise a rigid C-shaped member having an anterior end and a posterior end, a frontal positioner affixed to the anterior end of the C-shaped member, a guide cannula holder affixed to the posterior end of the C-shaped member, and a guide cannula, which guide cannula may be movably inserted into the guide cannula holder. Means to reversibly secure the guide cannula in the guide cannula holder may also be present. The guide cannula is typically a tubular shaft having a burr hole locator means affixed to one end of the shaft.

Methods for inserting a catheter into a ventricle in a brain of a human patient are also provided. The methods generally comprise identifying a frontal target site and a parieto-occipital entrance site, drilling a burr hole at the parieto-occipital entrance site, securing a device of the present invention on the patient, wherein the frontal positioner is placed at the frontal target site and the guide cannula is seated in the burr hole, and inserting the catheter through the guide cannula into the ventricle. The frontal target site may be marked by an adhesive ring to position the frontal positioner. Neuro-imaging studies may be used to determine the depth of the catheter placement and assess the contemplated catheter path. The catheter is generally inserted over a rigid stylet, such as, e.g., surgical wire.

Kits are also provided for practicing the methods of the present invention. The kits include ventricular catheters and stylets. Ring shaped pads for positioning the frontal positioner may also be included.

DETAILED DESCRIPTION OF THE SPECIFIC EMBODIMENTS

The present invention provides devices, methods and kits for parieto-occipital placement of ventricular catheters. The devices and methods of the present invention are superior to presently employed free-hand methods for parieto-occipital catheter placement and provide a safe alternative to frontal VP shunt placement and its associated problems.

In placement of a VP shunt, the ventricle may be cannulated by one of two approaches: frontal or parieto-occipital. The frontal approach is technically simpler for two reasons: the landmarks are easier to identify and the distance is shorter from the burr hole to the intraventricular target region. These reasons make the posterior (parieto-occipital) approach more hazardous. However, parieto-occipital placement also has certain advantages. For example, the cranial exit of the catheter is optimally situated for a continuous subcutaneous path to the abdomen, thus avoiding an additional incision. Further, parieto-occipital shunts may have less epileptic risk than frontal shunts, Dan et al., *J. Neurosurg.*, 65:19–21 (1986), found an incidence of 6.6% for parietal shunts and 54.5% for frontal shunts.

During a frontal approach, the nose and the ear provide simultaneous spatial references for the surgeon and both are visible during catheter placement. In contrast during a parieto-occipital approach, the target in the glabellar region is not visible to the surgeon during catheter placement when the surgeon is located posterior to the patient or, conversely, the burr hole and catheter are hidden if the surgeon is situated anteriorly. Because superficial landmarks are lacking, the catheter trajectory may only be estimated. This increases the likelihood of placement error.

An additional factor makes accurate parieto-occipital catheter placement more difficult. The distance between the entrance burr hole and the desired catheter position in the anterior horn of a lateral ventricle is significantly longer in the parieto-occipital approach than the frontal approach. The distance separating the tip of a misplaced catheter and its intended target depends both on the error in the trajectory angle and the distance the catheter travels. For a given error angle, the absolute distance by which the catheter tip misses the intended target increases linearly with the increasing length of the catheter pass. Thus for example, a 10 cm. parieto-occipital catheter passed in a straight line with a trajectory error angle of 5 degrees will have a final catheter tip position twice as far from the target as a 5 cm. frontal catheter with the same angle of error.

The present invention provides a means for significantly improving the accuracy of parieto-occipital catheter trajectory placement. When positioned on a patient, the device provides a linear trajectory between two surface landmarks, the burr hole and the frontal target site. The landmarks are chosen so that the linear catheter trajectory will pass through the frontal horn of a lateral ventricle. Thus, when the catheter is advanced along the trajectory defined by the present invention, the catheter will enter the anterior horn of a lateral ventricle and be properly positioned. In contrast, the traditional free-hand parieto-occipital approach relies on the surgeon's visuo-spatial skills to orient the catheter properly, increasing the risk of inaccurate placement and decreasing consistency.

Further, the present invention is both inexpensive and rapid, adding less than 5 minutes to the duration of the procedure. Thus, the present invention may minimize the morbidity secondary to VP shunt placement in a very cost-effective manner.

The devices of the present invention generally comprise a rigid C-shaped member having an anterior end and a posterior end, a frontal positioner affixed to the anterior end of the C-shaped member, a guide cannula holder affixed to the posterior end of the C-shaped member, and a guide cannula, which guide cannula may be movably inserted into the guide cannula holder. The devices may be used on any humans, regardless of age, sex, or size. The movable guide cannula allows for a single device to be used on patients having any head size.

The rigid C-shaped member may be constructed from a variety of different materials. Generally, the materials should be able to withstand temperatures in excess of 150° C. without deformation or loss of rigidity. This allows for the devices to be sterilized in an autoclave between uses. Generally, the devices will be constructed from surgical stainless steel or another metal. Alternatively, the devices may be constructed from plastics, nylon, vinyl, and the like.

Preferably, the C-shaped member will generally be formed from 1 piece of stock. Alternatively, the C-shaped member may be formed by rigidly affixing three or more segments to form a C-shaped frame. In either instance, it is preferred that the curvature producing the C-shape be greater than 90° in order to facilitate cleaning and sterilization. The cross-sectional shape of the C-shaped member is not critical and may vary, although the shape will generally be rectangular, square, or round. The cross-sectional dimension (diameter or diagonal, as appropriate for the shape) will usually be about 0.5 cm to 4 cm, more usually about 1 cm to 2 cm, and preferably about 1.25 cm. The cross-sectional size and shape will generally be chosen to provide a comfortable fit in the surgeon's hand during use.

The C-shaped member will have an anterior end and a posterior end. Generally, the shape of the anterior end and the posterior end will be symmetrical. The distance between the inner surfaces of the anterior and posterior ends will generally be about 25 cm to 50 cm, usually about 30 cm to 40 cm, and most preferably about 35 cm. Generally, the C-shaped member will have a segment without curvature to facilitate holding the device during use. The straight segment will generally be about 12 cm to 28 cm long. Alternatively, the C-shaped member may have an affixed handle or specialized curvature to aid manipulation and holding of the device by the surgeon.

A frontal positioner is affixed to the anterior end of the C-shaped member. The frontal positioner rests against a predetermined point or landmark on the patient's forehead during use. The frontal positioner is located on the inner surface of the C-shaped member in order to face the patient during use. Generally, the frontal positioner tapers toward the posterior end of the C-shaped member. Preferably, the frontal positioner is conical. The base of the cone abuts the inner surface of the C-shaped member. The apex of the cone is oriented toward the patient during use. The apex abuts the patient's forehead (or surgical drapes covering the forehead) at the frontal target site. Generally the apex will be slightly rounded. The frontal positioner is typically about 2 cm to 3 cm long. The cross-sectional dimension of the base of the frontal positioner is generally about the same size as the cross-sectional dimension of the C-shaped member.

The frontal positioner will generally be constructed from the same material as the C-shaped member, although it is not necessary so long as the frontal positioner withstands temperatures of at least 150° C. as described above. The frontal positioner is securely affixed to the inner surface of the C-shaped member. The frontal positioner may be thermally affixed (e.g., by welding or brazing metal components), mechanically affixed (e.g., by screws), by chemical adhesion, of the like. In some instances, the frontal positioner may be formed as a part of the C-shaped member.

A guide cannula holder is affixed to the posterior end of the C-shaped member. The guide cannula holder may be constructed of any of the materials suitable for use as the C-shaped member and affixed to the C-shaped member as described above. The guide cannula holder typically has an elongate configuration. The long axis is oriented parallel to the long axis of the C-shaped member. The guide cannula holder is generally about 5 cm to 12 cm in length. Often the guide cannula holder has a square cross-section with a diagonal dimension about 20–50% greater than the diagonal (or radial) dimension of the cross-section of the C-shaped member.

The guide cannula holder has a passage for insertion of the guide cannula running parallel to the long axis of the guide cannula holder. The passage allows for insertion of the guide cannula into the guide cannula holder. Typically, the diameter of the passage is about 4 mm to 8 mm, and in a preferred embodiment about 6.5 mm. While the guide cannula may move slidably in the passage, the long axis of the guide cannula is held stable. The guide cannula holder will often have a means for securing the guide cannula in a reversible manner. When secured, the guide cannula is not able to slide in the passage. The securing means is generally a set screw. The set screw is placed into a threaded sleeve that intersects the passage. When the guide cannula is in the guide cannula holder, the set screw may be tightened to contact and secure the guide cannula. When the set screw is loosened, the guide cannula may slide through the passage.

The guide cannula is a rigid tubular elongate body. The guide cannula is preferably constructed from surgical stainless steel, although rigid plastics, vinyls, and the like may also be employed. The guide cannula will generally be reusable. Therefore, the guide canula must be resistant to sterilization, such as autoclaving. Alternatively, the guide cannula may be intended for single uses. The outer diameter of the guide cannula is generally about 25 mm to about 7 mm, preferably about 6 mm. The inner diameter of the guide cannula must be of sufficient size to allow transit of a ventricular catheter. Generally, the inner diameter of the guide cannula is about 2 mm to 4 mm for use with adults and about 2 mm to 4 mm for use with children. The guide cannula is usually about 10 cm to 20 cm, preferably about 16 cm to 18 cm in length. When inserted in the guide cannula holder, the longitudinal axis of the guide cannula will generally be collinear with the longitudinal axis of the frontal positioner.

The guide cannula has two ends, an operator end and an occiput end. The occiput end is nearest the patient during use. An occipital burr hole locator is usually affixed to the occiput end of the guide cannula. The occipital burr hole locator provides a stopping means so that the guide cannula may not be accidently advanced into the brain. The occipital burr hole locator has a larger diameter than the guide cannula, typically about 1.5 cm to 4 cm, preferably about 2.5 cm to 3.5 cm. Conveniently, the occipital burr hole locator will have a portion that is cone shaped. The cone will taper away from the shaft of the guide cannula (toward the patient during use). Generally, the conical portion will be truncated and not come to a point at the apex. The conical portion provides a surface that can seat in the occipital burr hole. Seating the guide cannula may provide a means for securing the device to the patient during use. When seated, the occipital burr hole locator should not touch the brain. Alternatively, the occipital burr hole locator may have other shapes that can seat in a circular burr hole. Such shapes include, e.g., spherical, elliptical, and the like.

The present invention also provides methods for inserting a catheter into a ventricle in a brain of a human patient. The methods generally comprise identifying a frontal target site and a parieto-occipital entrance site, drilling a burr hole at the parieto-occipital entrance site, securing a device of the present invention on the patient, wherein the frontal positioner is placed at the frontal target site and the guide cannula is seated in the burr hole, and inserting the catheter through the guide cannula into the ventricle.

The frontal target site and parieto-occipital entrance site are generally identified by measurement from surface landmarks. In adults and older children, the frontal target site is generally about 1 cm superior to the supraorbital rim in the midline. The adult (and older child) parieto-occipital entrance site is generally about 7 cm superior to the inion and 3 cm lateral to the midline, ipsilateral to the target lateral ventricle. In infants and young children, the frontal target site is generally about 1 cm superior to the supraorbital rim in the midline and the parieto-occipital entrance site is generally about 3–4 cm above the inion and 2–3 cm lateral to midline, ipsilateral to the target lateral ventricle. Persons of skill will realize that in grossly altered anatomy (e.g., resulting congenital malformations, tumors, and head trauma), the frontal target site and the parieto-occipital entrance site may be in different locations. Preoperative neuro-imaging studies, such as computerized tomography, magnetic resonance imaging, contrast radiography (e.g., pneumoencephalogram or contrast-enhanced plain radiographs, sonograms, and the like) may be used to guide selection of alternative frontal target and parieto-occipital sites by methods well known in the art. The depth of catheter placement may also be determined by measurement from preoperative imaging studies.

Following identification of the frontal target site on the patient, a ring-shaped pad may be placed at the frontal target site to aid in holding the device of the present invention in place, as well as to mark the frontal target site. By "ring-shaped pad," it is meant a pad with a hole or depression located centrally. The hole or depression is typically about 5 mm in diameter. The ring-shaped pad will generally have an adhesive surface that may be applied to the patient's skin or surgical drapes overlying the frontal target site. Often, the ring-shaped pad may be fashioned from a surgical bovie pad by excising a centrally located circle or square.

Using standard surgical techniques, the cranium in the region of the parieto-occipital entrance site is exposed. The location of the parieto-occipital entrance site is identified and a burr hole drilled. Bleeding is controlled and the dura is incised and retracted exposing the pial surface. A device of the present invention having the guide cannula inserted in the guide cannula holder is placed on the patient. The frontal positioner is located at the frontal target site. The guide cannula is advanced out of the guide cannula holder until seated in the burr hole. The guide cannula may then be secured into place by a securing means on the guide cannula holder, if present. Alteratively, the guide cannula may be advanced to within about 1 cm to 1.5 cm from the outer surface of the skull and held in place by the surgeon (this allows direct visualization of penetration of the pia).

Once the device is seated or manually held in place, a ventricular catheter is advanced through the guide cannula. The catheter is advanced until it penetrates the ventricle and lies at the target position in the ventricle. Cerebro-spinal fluid will typically flow from the catheter when the tip is in the ventricle. Generally, the catheter is advanced with a rigid stylet present in the catheter. The rigid stylet aids in guiding the catheter on a straight path through the brain. The rigid stylet may be surgical wire cut to a length of about 30 cm to 40 cm. Eighteen gauge wire is preferred.

After the catheter has been properly positioned in the ventricle, the stylet is removed. If present, the securing means is loosened. The guide cannula is withdrawn from the burr hole and the device removed from the patient. The surgeon will generally hold the catheter in place during withdrawal of the guide cannula and removal of the device. The remainder of the procedure proceeds by standard techniques, such as described in Neurological Surgery 3rd ed. Ed. J. R. Youmans 1990 W. B. Saunders Co. Ch 41 pp 1277 Hydrocephalus in Adults, incorporated herein by reference.

Meticulous surgical technique should be employed as with all neurosurgical procedures. Both the bone and the dural edge may deflect the catheter from its intended course, so care must be taken to assure that the catheter is free from impingement at the pial surface. Also, the stylet must not be bent, as this may cause the catheter to deviate away from the target.

Kits for occipital placement of ventricular catheters employing the present invention are also provided. The kits generally comprise a ventricular catheter and a stylet. Suitable ventricular catheters are available from a variety of commercial sources, such as Codman Inc., 41 Pacella Park Dr., Randolph, MA 02368. As noted above, the stylet may be surgical wire, preferably 18 gauge. Alternatively, the stylet may be straight aluminum (or any other metal) hollow tubing with outer diameter$\leq$2 mm. The kits may also include a ring-shaped pad for marking the frontal target site as described above. The ring-shaped pad will typically have an adhesive surface to facilitate fixation during surgery.

Figure 1A:
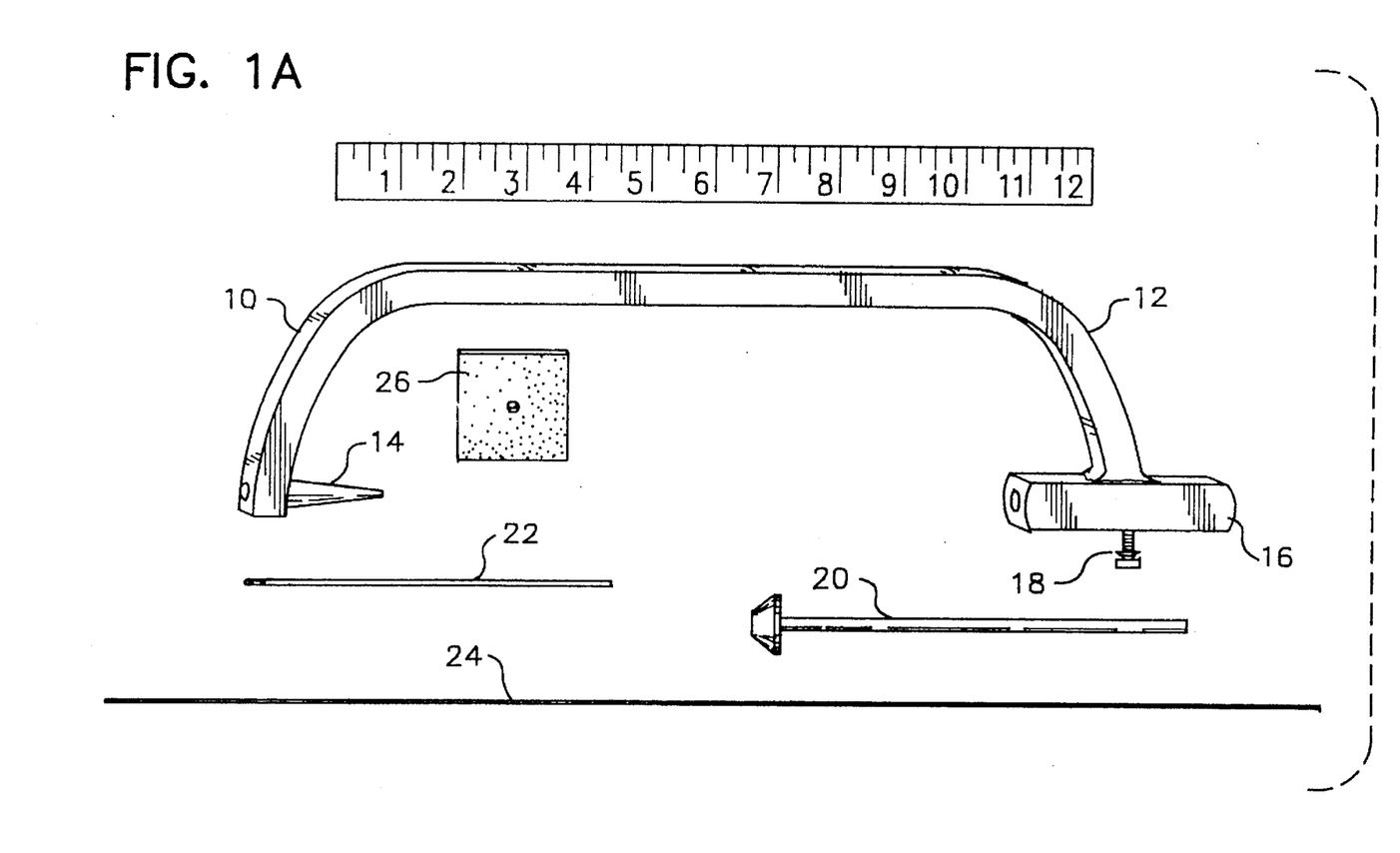
FIGS. 1A and 1B illustrate one embodiment of a device of the present invention.
Figure 1B:
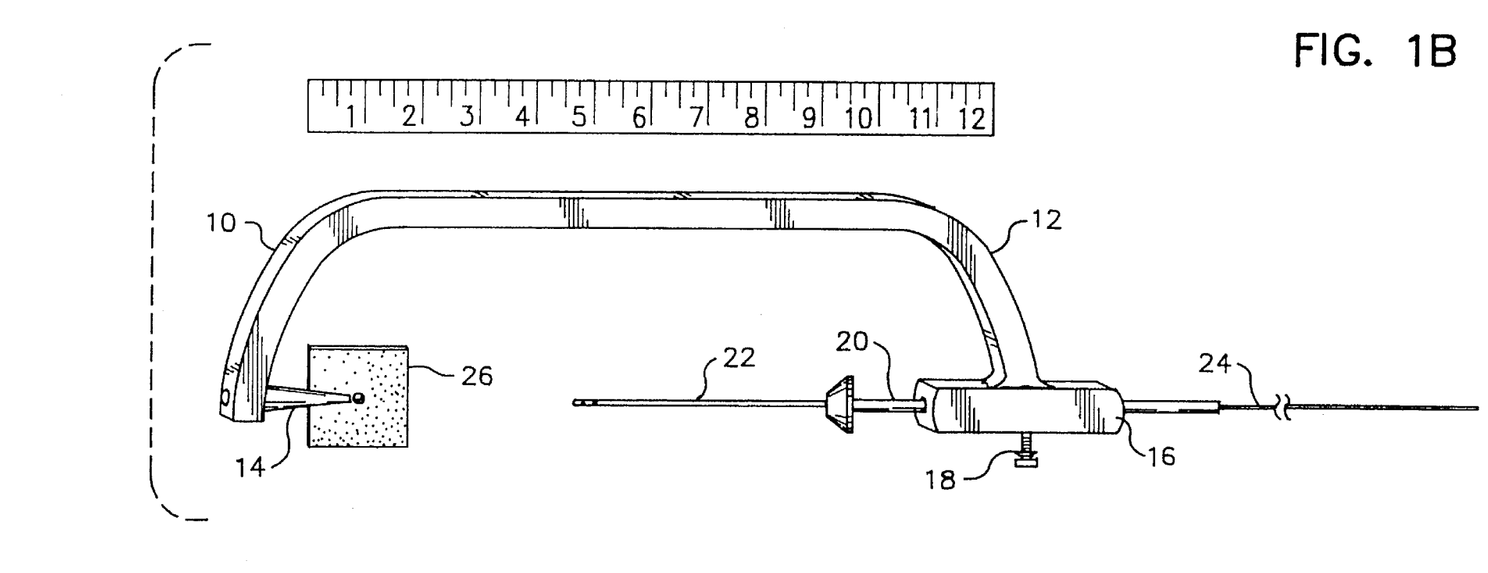

FIGS. 1A and 1B illustrate a device 10 of the present invention. The device 10 comprises a C-shaped member 12. A frontal positioner 14 is fixed to the anterior end of the C-shaped member 12. A guide cannula holder 16 is affixed to the posterior end of the C-shaped member 12. A set screw 18 is located in the guide cannula holder 16. FIG. 1A illustrates the guide cannula 20 outside of the guide cannula holder 16. A catheter 22 and surgical wire stylet 24 are also illustrated.

FIG. 1B illustrates the guide cannula 20, the catheter 22, and the surgical wire stylet 24 in the device as during use. The guide cannula 20 is in the guide cannula holder 16. The catheter 22 is in the guide cannula 20 and the surgical wire stylet 24 is in the catheter 22. A ring-shaped pad 26 is illustrated near the frontal positioner 14.

Figure 2A:
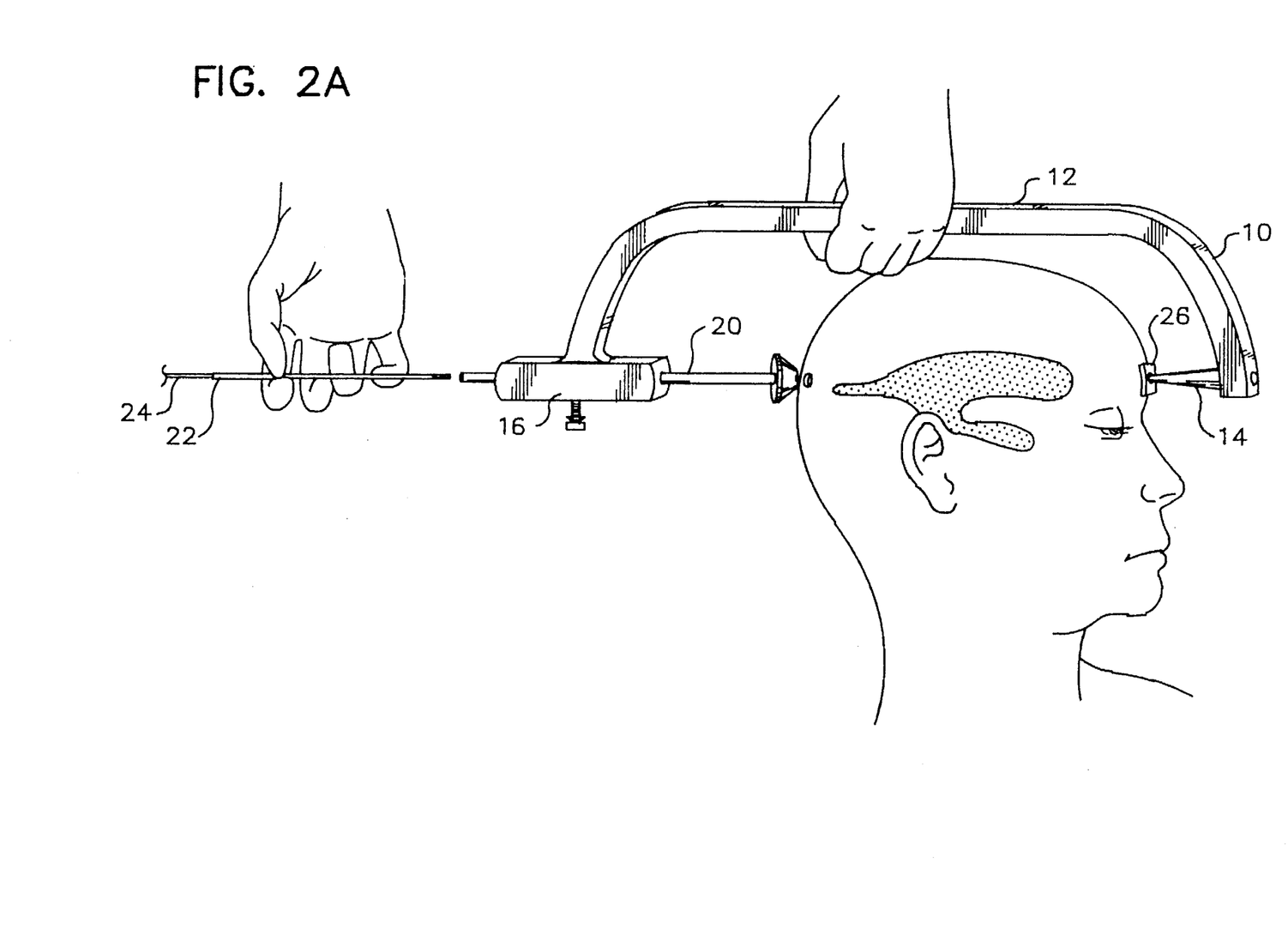
FIGS. 2A and 2B illustrate positioning of a catheter within a ventricle using a device of the present invention.
Figure 2B:
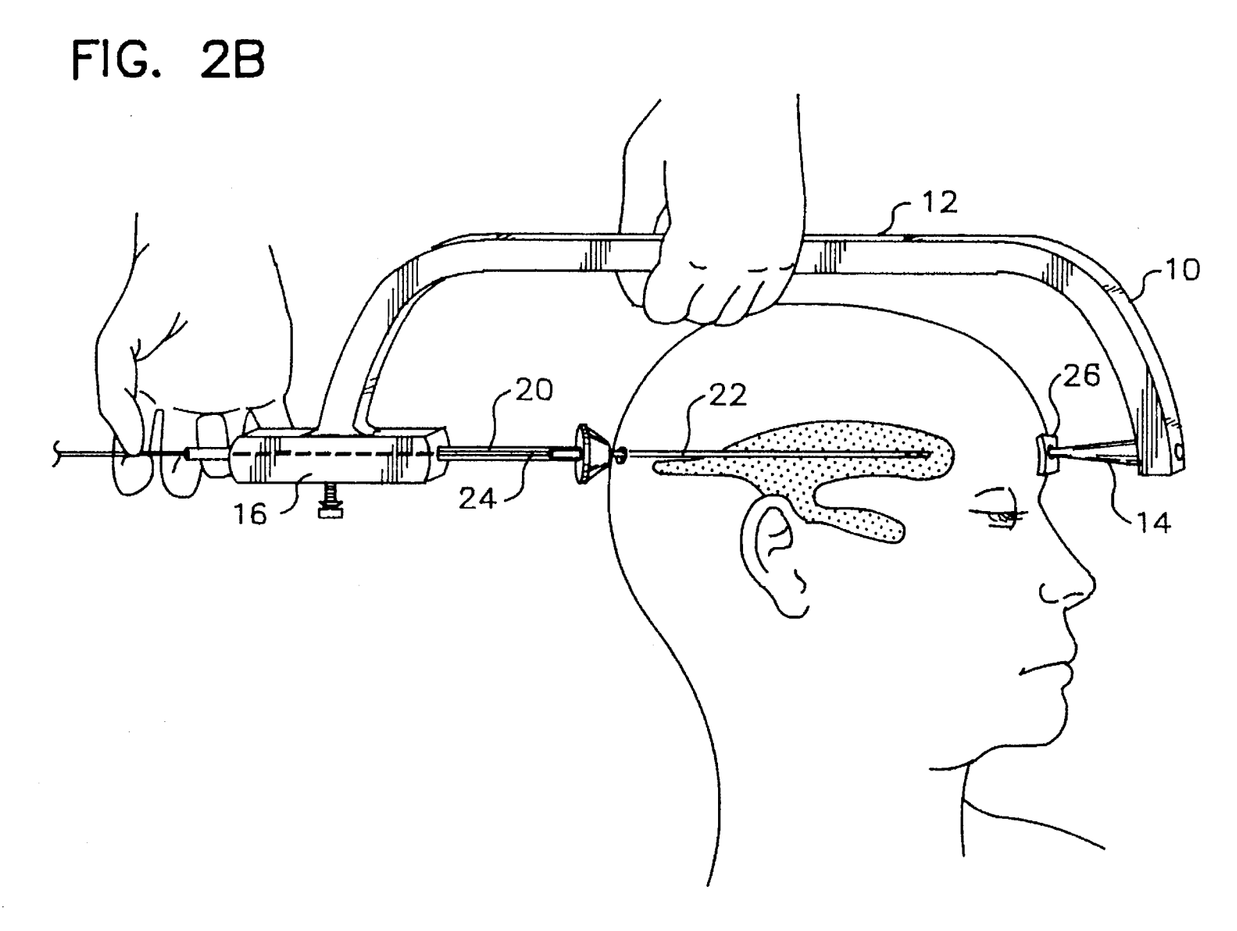

FIGS. 2A and 2B illustrate use of the present invention. The device 10 is present on the patient. The frontal positioner 14 is held by a ring-shaped pad 26. The surgeon is holding the C-shaped member 12. The guide cannula 20 is in place within the guide cannula holder 16. In FIG. 2A, the surgeon is holding the catheter 22 containing a stylet 24. In FIG. 2B, the catheter 22 is properly positioned and the surgeon is withdrawing the stylet 24.

EXAMPLES

Example 1

This example illustrates use of the devices and methods of the present invention in patients having hydrocephalus. The device provided a safe, effective, and efficient means for occipital placement of ventricular catheters.

Under institutional review board approval, a prospective clinical study of surgical use of the device of the present invention was initiated at the University of Washington affiliated hospitals. Patients seen with hydrocephalus over an 18 month period underwent parieto-occipital ventriculo-peritoneal shunt (VPS) placement utilizing the present device, absent contraindications to this surgical approach, such as recent occipital surgery. All patients with hydrocephalus were included, regardless of ventricular size. The clinical study was continued at the University of Iowa.

Operative records were employed to document the number of attempts necessary to achieve good catheter placement, as well as any intraoperative difficulties encountered. A post-operative CT scan was obtained prior to discharge to identify the position of the ventricular catheter. Correct placements were classified as those in which the tip of the catheter was placed in the anterior horn of the ipsilateral lateral ventricle.

Devices of the present invention were manufactured in the University of Washington (U.W.) and University of Iowa (U.I.) scientific instrument shops. The device was used on all patients regardless of head circumference. The devices were sterilized by autoclave prior to each use.

Each patient was positioned and prepped as for a standard parieto-occipital ventriculo-peritoneal shunt except that the forehead of each patient was covered by transparent adhesive drapes to allow visualization of the frontal target site located in the midline 1 cm. above the supraorbital rim. A modified Bovie cleaning pad (Baxter Healthcare Corporation, Deerfield, Il.), with an approximately 5 mm. by 5 mm. square cut in the center, was placed on the forehead with the hole directly over the target site. The location of the burr hole was imperative for successful use of the device of the present invention; in adults and older children, the burr hole was placed 7 cm. above the inion and 3 cm. lateral to the midline. In infants, the burr hole was made 3–4 cm. above the inion and 2–3 cm. lateral to the midline. A preoperative CT scan was used to identify anatomic anomalies and to estimate the depth of catheter placement needed to reach the frontal horn of the lateral ventricle.

After the burr hole was made and the dura opened, the device was positioned so that the anterior positioner rested in the opening in the Bovie pad and the adjustable guide cannula was positioned several millimeters external to the burr hole so the pial surface was visible. A standard 25 cm. ventricular catheter over a long, straight wire stylet was passed through the guide tube to the desired depth. The stylet was removed to confirm ventricular entry, the guide tube withdrawn and the device removed from the patient's head. The ventricular catheter was then attached to the distal portion of the shunt assembly (value and peritoneal catheter). The tip of the peritoneal catheter was placed into the peritoneal cavity and all wounds were then surgically closed.

The accuracy of free hand parieto-occipital catheter placement was determined by a retrospective review of all patients undergoing parieto-occipital ventriculoperitoneal shunt placement over a recent two year period at both UW and UI. Forty-three patient charts describing free hand procedures were reviewed, with particular attention paid to operative reports and post-operative studies to document shunt placement. On review, it was found that the operative notes often did not address the number of pass attempts made, making it difficult to compare to the present data. However, all patients underwent either AP and Lateral skull radiographs or CT scan post-operatively. Good catheter placement was defined as identification of the catheter tip in the ipsilateral frontal horn. The same CT criteria were used for catheter placement with the device of the present invention and free hand data.

Thirty-eight patients underwent parieto-occipital VP shunt placement using the device of the present invention. The patients ranged in age from 7 years to 82 years (average age 59.6 years). Fourteen of 38 patients (36.8%) had a diagnosis of subarachnoid hemorrhage (SAH), 11 (28.9%)

had normal pressure hydrocephalus (NPH), and 6 (15.8%) had traumatic brain injury (TBI). The remainder had a variety of diagnoses including tumors, vascular malformations, and chronic cerebrospinal fluid (CSF) leaks (Table 1).

In 34 of 38 operations (89.5%), the catheter was placed on the first pass using the device of the present invention. Poor flow (n=2) or no flow (n=2) of CSF was noted with the first catheter pass in four patients. Two of these cases were performed early in the series and the poor CSF flow resulted from incorrect placement of the posterior burr hole; this was corrected by placement of a second burr hole. The catheter was inadvertently deflected on a dural edge within the burr hole in one case. This was easily corrected by retracting the dural leaves with bipolar cautery. The fourth case occurred later in the series in a young patient with small ventricles and elevated intracranial pressure. Following placement of the catheter, a small volume of fluid was released under high pressure, after which spontaneous flow ceased. The catheter was removed and replaced with a second catheter without altering the position of the guide device, as the surgeon suspected that the catheter had become obstructed. The flow remained poor through the second catheter, but intraoperative pneumoencephalogram revealed good catheter position. Thus, the catheter was not replaced. Post-operative CT scan confirmed accurate catheter positioning and the patient subsequently made an uneventful recovery.

Post-operative CT scan demonstrated good catheter placement in 35 of 38 patients (92.0%), with the tip of the catheter being in the ipsilateral frontal horn of the lateral ventricle. The accuracy rate was significantly higher than noted in the retrospective series of free hand posterior catheter placements used as a control. Only 51.1% of the free-hand placement group had accurate catheter placement, a statistically significant difference (p<0.001). In two cases (5.3%), the catheter crossed the midline and was located in the contralateral ventricle. In one case (2.6%), a small hematoma developed along the catheter tract in the parietal lobe, although the catheter was in the correct position (Table 2).

Three patients died (7.9%); one, the first patient of the series, from a myocardial infarction three days following shunt placement and two from complications of their underlying diagnosis of subarachnoid hemorrhage. There were no shunt infections or malfunctions during the follow-up period of 2 months.

Forty-three patients who had undergone free hand parieto-occipital VP shunt placement at both institutions (UW and UI) were reviewed. The average age was 53 years and the most common diagnosis was NPH (13 of 43 patients, 30.2%), followed by SAH (11 of 43 patients or 25.6%) and tumors (10 of 43 patients, or 23.3%). Five patients (11.3%) had traumatic brain injury as the etiology of their hydrocephalus and the remainder had a variety of causes (Table 1). Accurate operative data was not available for these patients, but all had post operative radiographic studies to determine catheter position: thirty-seven (86%) had CT scans and 6 (14%) had AP and lateral skull radiographs.

Twenty-two patients (51.1%) had accurate placement of the ventricular catheter, while 21 (48.9%) did not. In seventeen of these latter patients (39.5% of all patients), the catheter crossed the midline to rest in the contralateral anterior horn. In one patient, the catheter traversed the ipsilateral basal ganglia to end in the frontal horn and, in one patient, the catheter was passed too far, with the tip in the periventricular frontal lobe. A single catheter placement was too shallow ending at the foramen of Munro (Table 2). None of these patients suffered any immediate clinical consequences from the positions of the catheters; however, long term follow-up was not available for further assessment.

A comparison of the two groups revealed no statistically significant difference in the mean age or the diagnoses (p>0.05). The frequency of optimal catheter placement was compared between the free hand catheter placement group and the group undergoing placement with the device of the present invention. By Chi square analysis, the difference in accurate placement in the device group (92.0%) versus the free hand group (51.1%) was statistically significant ($X^2 = 14.31$, p<0.001).

TABLE 1

A comparison of the etiologies of hydrocephalus in the device and the free-hand groups

| DIAGNOSIS | DEVICE | FREE HAND |
|---|---|---|
| Subarachnoid Hemorrhage | 14 (36.8%) | 11 (25.6%) |
| Normal Pressure Hydrocephalus | 11 (28.9%) | 13 (30.2%) |
| Traumatic Brain Injury | 6 (15.8%) | 5 (11.3%) |
| Miscellaneous, including tumors | 7 (18.5%) | 14 (32.9%) |
| TOTAL | 38 | 43 |

TABLE 2

A comparison of catheter tip placement in the device and the free-hand groups

| POSITION | DEVICE | FREE HAND |
|---|---|---|
| Correct position | 35 (92.0%) | 22 (51.1%) |
| Crosses Midline | 2 (5.3%) | 17 (39.5%) |
| Hematoma | 1 (2.6%) | 0 |
| Parenchymal | 0 | 3 (7.0%) |
| TOTAL | 38 | 43 |

All publications mentioned in this specification are herein incorporated by reference into the specification to the same extent as if each individual publication, patent or patent application was specifically and individually indicated to be incorporated herein by reference.

Although the foregoing invention has been described in some detail by way of illustration and example for purposes of clarity of understanding, it will be obvious that certain changes and modifications may be practiced within the scope of the appended claims.

What is claimed is:

1. A device for occipital placement of a ventricular catheter in a brain, comprising:
   a rigid C-shaped member having an anterior end and a posterior end;
   a frontal positioner affixed to the anterior end of the C-shaped member;
   a guide cannula holder affixed to the posterior end of the C-shaped member; and
   a guide cannula, which guide cannula may be movably inserted into the guide cannula holder, wherein the guide cannula comprises a tubular shaft having an occiput end, an operator end, and an occipital burr hole locator affixed to the occiput end.

2. The device of claim 1 wherein the occipital burr hole locator comprises a conical portion tapering away from the shaft.

3. A method for inserting a catheter into a ventricle in a brain of a human patient comprising:

identifying a frontal target site and a parieto-occipital entrance site;

drilling a burr hole at the parieto-occipital entrance site;

securing a device which comprises a rigid C-shaped member having an anterior end and a posterior end, a non-penetrating frontal positioner affixed to the anterior end of the C-shaped member, a guide cannula holder affixed to the posterior end of the C-shaped member, and a guide cannula, which guide cannula may be movably inserted into the guide cannula holder on the patient, wherein the frontal positioner is placed at the frontal target site and the guide cannula is seated in the burr hole; and inserting the catheter through the guide cannula into the ventricle.

4. The method of claim 3, further comprising obtaining a neuro-imaging study and identifying therefrom the depth of catheter placement required to reach the ventricle.

5. The method of claim 3, wherein the patient is an adult and the burr hole is placed approximately 7 cm superior to the inion and approximately 3 cm lateral to the midline, and the frontal target site is in the midline and approximately 1 cm superior to the supraorbital rim.

6. The method of claim 3, wherein the frontal target site is marked with an adhesive ring.

7. The method of claim 3, wherein the catheter is inserted over a rigid stylet.

8. The method of claim 7, wherein the rigid stylet is surgical wire.

9. The method of claim 8, wherein the surgical wire is 18 gauge.

* * * * *